(12) United States Patent
Kronvall

(10) Patent No.: US 7,465,559 B2
(45) Date of Patent: Dec. 16, 2008

(54) METHOD FOR CALIBRATING ANTIBIOTIC DISK DIFFUSION TESTING OF MICROORGANISMS

(75) Inventor: Goran Kronvall, Taby (SE)

(73) Assignee: Bioscand AB, Taby (SE)

( * ) Notice: Subject to any disclaimer, the term of this patent is extended or adjusted under 35 U.S.C. 154(b) by 395 days.

(21) Appl. No.: 10/474,488

(22) PCT Filed: Apr. 8, 2002

(86) PCT No.: PCT/SE02/00688

§ 371 (c)(1), (2), (4) Date: Apr. 19, 2004

(87) PCT Pub. No.: WO02/083935

PCT Pub. Date: Oct. 24, 2002

(65) Prior Publication Data

US 2004/0175779 A1     Sep. 9, 2004

(30) Foreign Application Priority Data

Apr. 10, 2001   (SE)   .................... 0101251

(51) Int. Cl.
- C12Q 1/18     (2006.01)
- G06F 19/00    (2006.01)
- G01N 33/48    (2006.01)
- G01N 33/50    (2006.01)

(52) U.S. Cl. .......................... 435/32; 702/19
(58) Field of Classification Search .................. 435/32; 702/19
See application file for complete search history.

(56) References Cited

OTHER PUBLICATIONS

APMIS, vol. 99, 1991, Göran Kronvall et al: "Compaison of 30 ug and 120 ug gentamicin disks for the prediction of gentamicin resistance in *Enterococcus faccalis*", pp. 887-892, see pp. 889-891.
Journal of Clinical Microbiology, vol. 16, No. 5, 1982, Göran Kronvall: "Analysis of a Single Reference Strain for Determination of Gentamicin Regression Line Constants and Inhibition Zone Diameter Breakpoints in Quality Control of Disk Diffusion Antibiotic Susceptibility Testing", pp. 784-793.
Antimicrobial Agents and Chemotherapy, vol. 32, No. 10, 1988, Göran Kronvall et al: "Laboratory-and Species-Specific Interpretive Breakpoints for Disk Diffusion Tests of Chloramphenicol Susceptibility of Haemophilus influenzae", pp. 1484-1489.
APMIS, vol. 99, 1991, Göran Kronvall et al: "Antibiotic disk diffusion testing revisted, Single strain regression analysis", pp. 295-306.
Scand J. Infect. Dis. Suppl., vol. 105, 1997, Gunnar Kahlmeter et al: "Antimicrobial Susceptibility Testing in Sweden. IV. Quality Assurance", pp. 24-31.
Scand J. Infect. Dis. Suppl., vol. 105, 1997, Barbro Olsson-Liljequist et al: "Antimicrobial Susceptibility Testing in Sweden. III. Methodology for Susceptbility Testing", pp. 13-23.
Scand J. Infect. Dis. Suppl., vol. 105, 1997, Signe Ringertz et al: "Antimicrobial Susceptibility Testing in Sweden. II. Species-related Zone Diameter Breakpoints to Avoid Interpretive Errors and Guard Against Unrecognized Evolution of Resistance", pp. 8-12.

*Primary Examiner*—Jon P Weber
*Assistant Examiner*—Kailash C Srivastava
(74) *Attorney, Agent, or Firm*—Merchant & Gould P.C.

(57) ABSTRACT

A method for calibrating antimicrobic susceptibility testings of microorganisms comprises the steps of creating a histogram with a high response side and a low response side of isolates from a microbial species, which may contain resistant strains against an antimicrobial agent, calculating from the high response side of the histogram at least one statistical parameter, and defining a limit for susceptibility interpretation and comparative analysis of antimicrobic resistance, which is based on the statistical parameter. This limit separates susceptible strains from resistant strains against an antimicrobial agent.

21 Claims, 3 Drawing Sheets

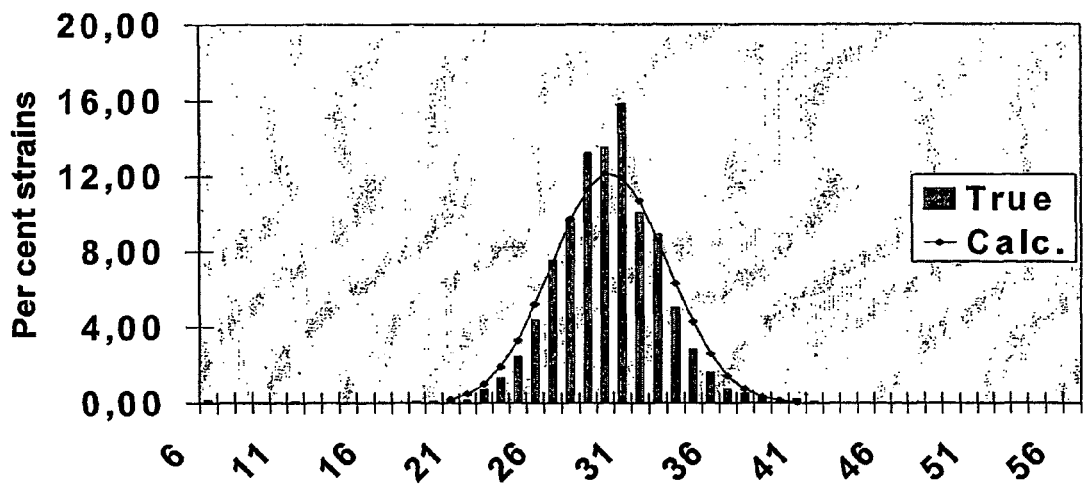
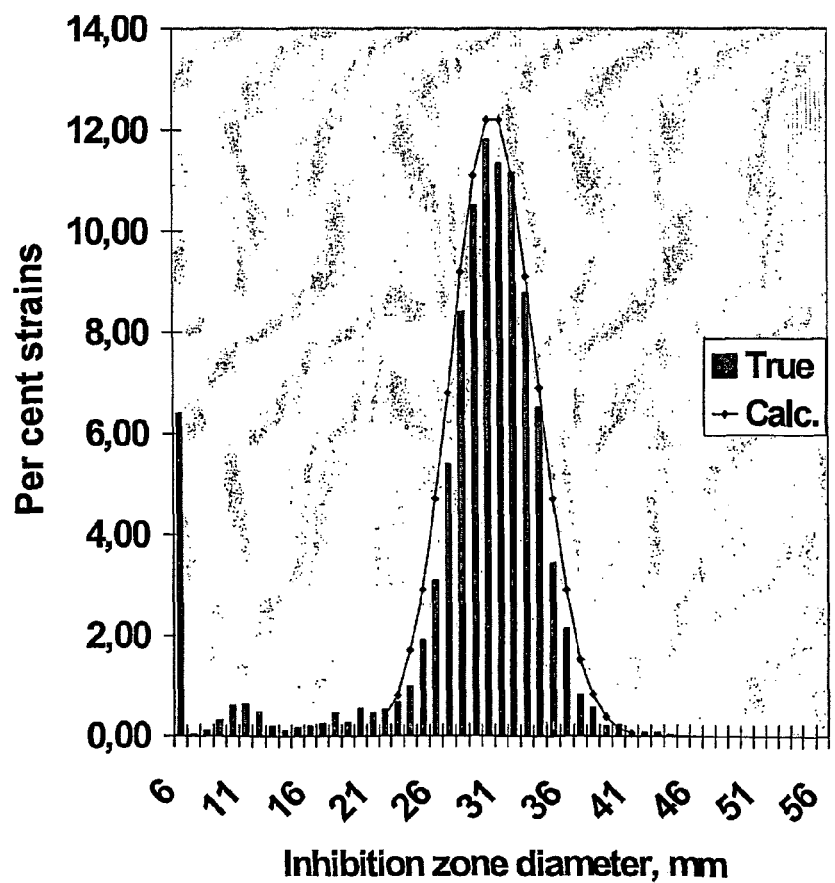

METHOD FOR CALIBRATING ANTIBIOTIC DISK DIFFUSION TESTING OF MICROORGANISMS

This application claims priority to PCT/SE02/00688 filed 8 Apr. 2002 and to Swedish Application Ser. No. 010125 1-7 filed on April 2001.

The present invention relates to the interpretion of antimicrobic resistance in routine susceptibility tests. More precisely, the invention relates to a method for calibrating antimicrobic susceptibility testings of microorganisms.

BACKGROUND

Antibiotic resistance surveillance becomes more and more important in a global situation of increased occurrence and spread of resistance genes among bacterial pathogens. National as well as international surveillance of antibiotic resistance is thus urgently needed in the present increase of resistance worldwide.

Antimicrobial susceptibility testing (AST) constitutes one of the most important methods of analysis in a clinical microbiology laboratory. Correct information regarding the most appropriate antimicrobial agent(s) to be used as empirical therapy in for example an acute clinical situation of an infected patient requires thorough knowledge of the antimicrobial susceptibility levels in relation to the bacterial species and the type of infection in question.

In addition, when a causative bacterial strain has been isolated from the site of infection the antimicrobial test results provide a rational basis for either continued therapy or a change to a more effective drug.

Different types of susceptibility tests can be used to test the antimicrobic susceptibility of a microorganism. One type of susceptibility test is the disk diffusion test. This is a standardized test, in which a plate containing a growth medium in agar gel is inoculated with a microbial isolate and one or more disks impregnated with fixed concentrations of antibiotics are placed thereon. After appropriate incubation, the diameter of zones of inhibition around the disks (if present) are registered in order to determine the sensitivity of the inoculated microorganism to the particular antimicrobial agent impregnated in each disk.

Another type of susceptibility test is the broth microdilution test. In this type of test, dilutions of antibiotics are prepared in tubes or microwells. Each tube or well with various concentrations of antibiotics, usually as a twofold dilution series, is inoculated with a standardized suspension of a particular microorganism. After incubation, the wells or tubes are examined for turbidity, haze and/or pellet and compared with a growth control as well as a non-inoculated control. The minimum concentration of antimicrobial agent that prevents visible microbial growth is calculated as the Minimal Inhibitory Concentration (MIC).

In spite of the availability for several years of automated microdilution methods, the disk diffusion method is still the most widely used susceptibility testing procedure in most countries. The test is performed according to some standardized methodology issued by a reference group, such as NCCLS (National Committee for Clinical Laboratory Standards), SRGA (Swedish Reference Group for Antibiotics), the French "Comité de l'Antibiogramme de la Société Francaise de Microbiologie", the British "Working Party on Antibiotic Sensitivity Testing of the British Society for Antimicrobial Chemotherapy", the Australian "ASIG Antimicrobials Special Interest Group", the German DIN group, etc.

The results of this test are semi-quantitative. In. 1979 the SRGA introduced the 3 susceptibility categories which are still in use today: S (susceptible), I (intermediate) and R (resistant) in dependence of the size of the inhibition zone.

However, the definitions and interpretive criteria for resistance vary with the guidelines adhered to as do those test results which are influenced by differences in test performance. The differences are particularly paramount for disk test results, which means that the majority of antibiotic susceptibility test results cannot be utilized for surveillance purposes.

Most surveillance efforts have relied on MIC tests because of the higher accuracy of such methods. The adherence to disk diffusion standards are often incomplete and the results unreliable. In one investigation using the disk method, all participating laboratories sent their bacterial isolates to one single laboratory where the disk tests were performed in order to ensure comparable results from the different geographical regions. Such an approach will be impossible if resistance surveillance is to be performed on a larger scale globally.

In general, organisms are considered susceptible to an antibiotic when they are inhibited by concentrations easily achieved in vivo and when the clinical efficacy has been documented. This implicates a correlation between the MIC and the clinical outcome. Similarly, organisms are termed resistant when concentrations required for inhibition are higher than those easily obtained in vivo, indicating that treatment with this antibiotic is not likely to be successful.

The statistical parameters for the inhibition zones obtained for individual bacterial species have been investigated (Kronvall et al., APMIS 99:887-892, 1991). At this time the bacterial species studied did not exhibit a considerable resistance to the antibiotic of choice, gentamicin. In order to be able to study a homogenous population any resistant outliers were eliminated, and the statistical parameters were only determined for those strains which belonged to the susceptible population.

When antibiotic susceptibility test results, such as inhibition zone diameter values, are analyzed separately for each antibiotic and bacterial species, including resistant strains, some special features become apparent. The position of a normal wild-type population of zone diameters in a given laboratory will stay remarkably stable over the years, reflecting the stability of a routine method in daily use. However, when results are compared between different laboratories, the position of a normal population might vary considerably. These inter-laboratory differences are the main reason for the relative lack of accuracy of the disk diffusion test.

One approach to solve the problem of interlaboratory variation has been to introduce a reference or control strain, which serves as a calibrator strain. Control strains are recommended by reference authorities for quality control and therefore such strains are usually already available in the laboratory.

A calibration is a regular procedure in any clinical chemistry test and involves the use of a calibrator with a known concentration of the substance to be measured. The calibration of the test in the individual laboratory using their own equipment and reagents is then controlled using control samples, either internal controls or from an external quality control agency.

One method for calibration of the disk diffusion test is called "reference strain corrected breakpoints" (or "control strain peak correction") and requires the regular testing of an international reference strain in the laboratory (Kronvall et al., Antimicrob. Agents Chemother. 32:1484, 1988). The position of the zone diameter peak in the reference laboratory has to be known and the difference in mm value from this peak value to the interpretive break-points can be calculated. A similar relation should exist in the individual laboratory between its control peak value and the breakpoints, which should be adjusted accordingly. This method improved the accuracy of the disk test by reducing false-resistant interpretations from 4.4% to 2.3%.

A further improvement was obtained by using a second method, single strain regression analysis (Kronvall, J. Clin. Microbiol. 16:784, 1982). This method, called SRA, provides a calibration of the test, which is truly species-related and laboratory-specific. However, it both requires especially prepared disks with different disk potencies and computer programs for the calculations. This method further reduced false-resistant results down to 0.14% in the studies referred to above.

SUMMARY

The purpose of the invention is to achieve a method for calibrating antimicrobic susceptibility testings of microorganisms whereby the above-mentioned problems are eliminated.

Normalized or standardized interpretation of antibiotic resistance in bacteria from disk diffusion test results should relate to some stable characteristic of these test results. The position in the zone diameter histogram of the normal population of susceptible or wild type strains is such a stable characteristic that is available in every laboratory. The position of a single reference or control strain—which is tested repeatedly in the same manner as clinical isolates of the same or similar species—also represents such a stable characteristic which can form a basis for an internal calibration for normalization or standardization of interpretation of antimicrobic susceptibility/resistance.

The inventive method comprises an interpretation of a conventional histogram of in vitro susceptibility testings with isolates from a microbial species, which may contain resistant strains against an antimicrobial agent. The susceptibility test data are plotted on the y-axis and primary test measurement data for the antimicrobial agent are plotted on the x-axis. The susceptibility test data can be plotted as number of isolates or as percent isolates of microbial species.

BRIEF DESCRIPTION OF THE DRAWINGS

FIG. 3 shows the histogram of FIG. 1 with interposed calculated curve.

FIG. 4 shows the histogram of FIG. 2 with interposed calculated curve.

DETAILED DESCRIPTION

Figure 1:
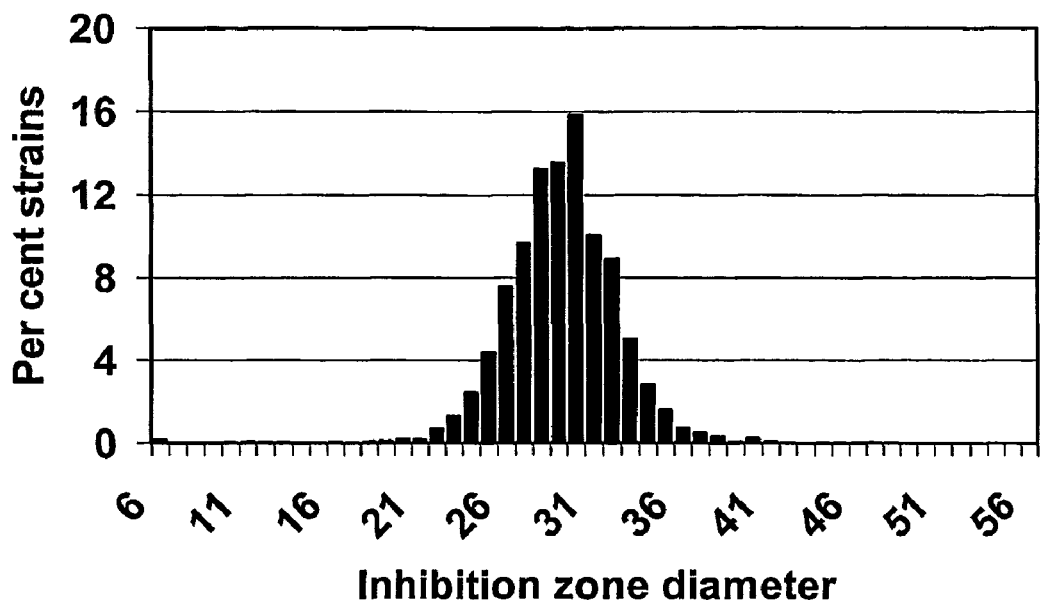
FIG. 1 shows a histogram of *Escherichia coli* isolates against norflaxacin.

The microbial species to be tested can be any cultivable microorganism, such as a bacterial species or a fungal species. In order to obtain species-related and laboratory-related interpretive breakpoints, a histogram of for example clinical isolates can be used. The method is especially suitable for analyzing inhibition zone diameters from disk diffusion tests with clinical isolates from a bacterial species, which may contain resistant strains against an antibiotic. Thus, no outliers are excluded. The number of isolates or percent isolates are plotted on the y-axis and the growth inhibition zone diameter values from paper disks impregnated with the antibiotic are plotted on the x-axis. When the method of O'Brien et al. (J. Am. Med. Assoc. 210:84, 1969) is used, histograms are obtained with percent isolates on the y-axis and zone diameter values from 6 mm (paper disk diameter) to 60 mm on the x-axis. However, the inventive method is equally well adapted for a microdilution tests, the concentration data being minimal inhibitory concentrations. All data can be computerized.

The basis for the present invention relates to a reconstruction of the original population which is susceptible to the antibiotic tested. In this connection certain relevant features of a corresponding histogram of isolates are utilized. When for example zone diameter histograms are produced for individual bacterial species and antibiotics, the distribution of zone diameter values will be rather restricted, and a homogeneous population will be formed for the naturally susceptible isolates without resistance. The high zone side of the normal population of susceptible strains therefore remains unchanged by the occurrence of resistant isolates. This provides the internal reference which makes histograms for the same combination of antimicrobial and bacterial species from any laboratory comparable. When clinical isolates of any combination of antibiotic and individual bacterial species are analyzed similarly, the position of the normally susceptible wild-type strains is unchanged whereas the resistant or intermediately resistant strains form more or less well defined populations at the lower end of the zone diameter spectrum.

When a homogeneous wild-type population of isolates or strains of a given species is analyzed by means of parametric and non-parametric methods populations are obtained which are slightly peaked and skewed towards higher inhibition zone diameter values as compared to the Gaussian distribution. The homogeneity is relative, but for the invention, they can be regarded as homogeneous. The resulting zones of inhibition exhibit a restricted range of values, which approximate a normal distribution (standard Gaussian distribution). However, the invention also applies to other kinds of probability distributions. Parametric tests, such as mean values and standard deviations, can therefore be used with negligible errors in order to describe the distribution. Thus, a probability distribution can be calculated from the histogram, and from this probability distribution at least one statistical parameter is calculated which can be used as an internal calibration of the disk diffusion test on the bacterial species examined. Then a susceptibility interpretation and a comparative analysis of antibiotic resistance can be accomplished. Parametric criteria can then be introduced in order to define interpretative breakpoints.

Such a normal population or a similar population of a control strain thus has the basic characteristics for any given combination of microbial species and antimicrobial agent. A limit for susceptibility interpretation and comparative analysis of antimicrobic resistance, e.g. normalized resistance breakpoint, can then be determined in several different ways.

According to the invention, at least one statistical parameter is calculated from the high response side of a histogram, preferably the upper part thereof. Such a statistical parameter of the histogram can be a peak value in the susceptible range, which can serve as an indicator of the normal population. Thus, the position of a normal population with no resistant isolates in a zone diameter histogram can be calculated as the mean value of the zone diameters. Alternatively, this position can be determined as the zone diameter with the maximum number of isolates. The median value can also be used for this purpose.

A limit for susceptibility interpretation and comparative analysis of antimicrobic resistance can then be defined, which is based on the statistical parameter taken from that part of the histogram only which comprises the high zone diameters. Susceptibility zone breakpoints for S, R, or I, respectively, can for example be obtained by subtracting defined millimeter values from the median value or the arithmetic mean.

Thus, when the peak position has been established in an individual laboratory for the normal population of strains of a given species tested against an antibiotic, then a normalized breakpoint for resistance can be determined in several ways. The peak position can simply be subtracted with a specific figure. This figure should be different for different antibiotics and should represent a normal limit for the susceptible normal population. This figure for subtraction adjustment can also be a function of the normal peak position.

However, it is preferred that the position of the peak between a high zone diameter distribution side and a low zone diameter distribution side (or corresponding high and low MIC values) is determined by means of more mathemtically precise methods. This also applies to the determination of a standard deviation.

In this case, the inventive method utilizes the observation that when antimicrobic resistance to an antimicrobial agent occurs among strains of a certain species the configuration of the histogram will change. Those isolates, which exhibit resistance, will inevitably produce smaller zones of inhibition, and they will often aggregate in populations separate from the original, normal population. Sometimes, they will also form a shoulder on the lower side of the normal population.

In other words, the acquisition of antimicrobic resistance genes or mutations reflect evolution in that isolates are always produced having inhibition zones (or MIC values), which are smaller (or larger) than those of the normal wild-type population. This means that in corresponding histograms the part representing the high zone values to the peak will always be unaffected by the development of resistance. Consequently, if this part can be properly characterized, then a hypothetical normal population of strains can be reconstructed in spite of the development of resistant isolates. An accurate characterization of this hypothetical normal population in a histogram of isolates from a microbial species—which may contain resistant strains against an antimicrobial agent—then makes it possible to estimate the number of strains which deviate from this population. Thus, a normalized way of defining antibiotic resistance is provided, which can be utilized for comparative surveillance purposes.

Such a normalization (or in this connection standardization) of a probability distribution has primarily a comparative purpose. It should not be confused with the interpretation into susceptibility categories, which a laboratory has to perform in order to provide a report to the requesting physician. In this case, an interpretation is performed according to the standardization of the methodology issued by a reference authority. The present method of normalization is intended to provide a uniform identification of resistance irrespective of the methodological standard used in the laboratory. Thus, by using the method for calibrating antimicrobic susceptibility testings of microorganisms according to the invention, a basis is provided for analyzing disk diffusion test results world-wide, levels of antibiotic resistance being compared.

The two parameters, which have to be characterized, are the peak of the normal population and the upper curve of increasing numbers of strains up to this peak. A normalized Gaussian distribution of a theoretical normal population can then be construed from the position of the zone diameter peak, the high zone diameter distribution side, and its mirror image. Such a normalized Gaussian distribution can be construed graphically by means of graphical models, such as undirected graphical models or directed graphical models. Such models are known by the skilled man within the arts of probability theory and graph theory.

However, a preferred way of defining a position of the zone diameter peak between a high zone diameter distribution side and a low zone diameter distribution side is described below for a normalized Gaussian distribution of a theoretical normal population. In this procedure, a total number for the theoretical normal population is construed.

Firstly, a slope is calculated for a line through the percent isolates of adjacent zone diameter values. Preferably, this is performed by starting on the high zone diameter distribution side of the histogram.

Secondly, a shift in slope direction is detected. The zone diameter value for this shift then represents the position of the zone diameter peak, the mean value of the zone diameters being defined.

Thirdly, the sum of half the number of isolates at the position now defined plus the number of isolates having higher zone diameter values is then calculated, and this sum is then doubled. In this way, the total number of isolates can be calculated for the theoretical normal population, i.e. for the high zone diameter distribution side from the middle of the position of the zone diameter peak and the mirror image thereof. Of course, a total percentage of isolates for a histogram can be calculated in a similar way.

In a preferred embodiment of the invention a computer program first checks the histogram from the uppermost zone values, weighted moving averages being calculated. Such averages can be determined by using strain numbers for two or more zone diameters. In order to make the test sensitive enough two zone averages are preferred. However, a better average is obtained if more zone data are included, but the detection of a shift from increasing averages towards a decreasing value then becomes less sensitive. It is also preferred that an increasing average is immediately followed by two decreasing average values in sequence, the position of the zone diameter peak being accurately established.

Of course, the calculation of averages can also be changed. For example, in laboratories with less precision an average should be calculated on three or four values instead of two.

When the computer program has registered a shift as described, the previous zone diameter is taken as the peak, i.e. the zone diameter of both the previous higher average and the last and lower average. With a weighted average including data for more than two zone diameter values, the zone diameter taken as the peak is shifted further up. The program then calculates the number of isolates with zone diameters higher than this peak zone plus half of the number of isolates at the peak zone diameter value. This total number represents the theoretical half of the normal population.

After resolving the total number for theoretical normal population, the normalized Gaussian distribution of the theoretical normal population has to be determined. A preferred procedure is described below. Firstly, for each zone diameter value on the upper half of the normal population a percentage value is calculated as percent of the theoretical total number.

Secondly, an accumulated percentage value is calculated for each number of isolates (or percent isolates) on this high zone diameter distribution side of the upper half of the normal population.

These percentage values can be estimated by commencing from isolates having the highest zone diameter values and then add up the number of accumulated isolates. The corresponding percentage of the theoretical total number is then calculated. Preferably, the order of these accumulated percentages values are then reversed, i.e. in the direction 100% to 0%.

Thirdly, a linearized transformation of these accumulated percentage values against the zone diameter values is performed. Such a transformation is performed in order to transform a curvilinear relationship to a linear relationship.

Preferably, a probit transformation is utilized, in which the reversed accumulated percentages are converted to probit-values. This can be accomplished by using a computer having a program for such conversion purposes.

At last, the equation constants are calculated for the linear relationship between the probit values and zone diameters. Preferably, this calculation is performed by using the least squares method.

When the linear relationship has been determined for the probit transformed percentage values against the inhibition zone values, the standard deviation (SD) can be calculated from the probit transformation. In this connection, the center of the linear relationship is probit 5.0, which corresponds to the mean. The difference between the zone value for probit 6.0 and this mean then represents 1 SD.

Alternatively, a theoretical curve can be calculated from the normalized Gaussian distribution. For this calculation the percentages for the in-between zone values (i.e. 30.5, 31.5, 32.5, etc.) can be used, and the values of the difference in percent are then used in order to plot a theoretical Gaussian distribution of the histogram for the normal population of strains. Then the mean value and the standard deviation can be calculated.

EXAMPLES

The invention will now be further described and illustrated by reference to the following examples. It should be noted, however, that these examples should not be construed as limiting the invention in any way.

Example 1

Evaluation of Antibiotic Resistance with Time

FIG. 1 shows a histogram of 1988 from Karolinska hospital in Sweden, in which histogram *Escherichia coli* isolates were tested against norfloxacin (disk content 10 μg). It can be seen that the zone diameter values for these clinical isolates cluster around 29-30 mm with a distribution of ±8 mm.

Figure 2:
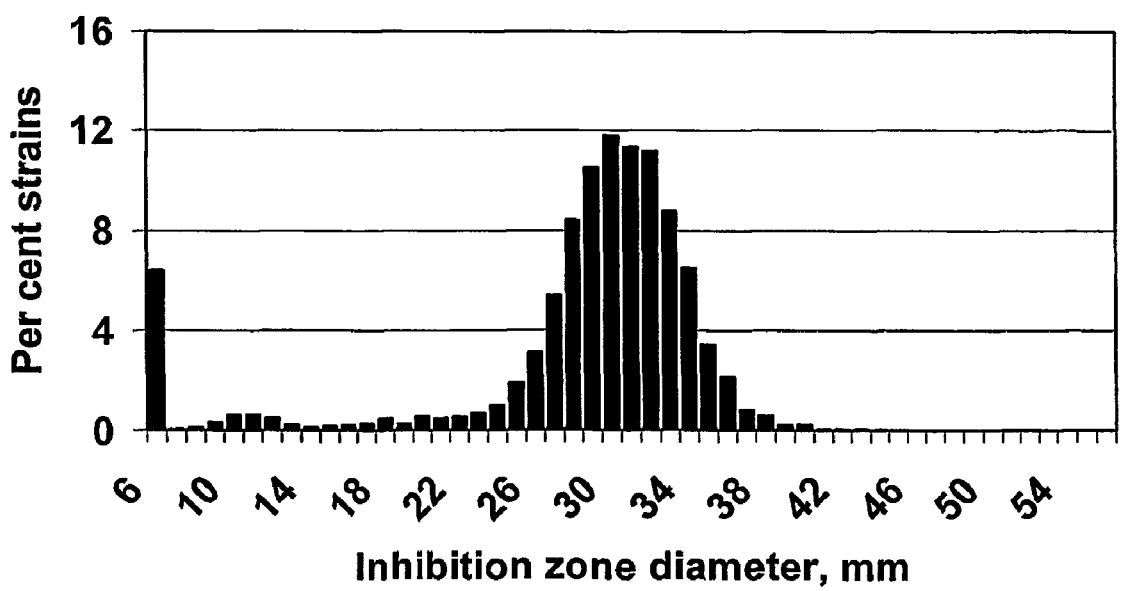
FIG. 2 is histogram similar to FIG. 1, except taken eleven years later.

The results from 1988 in FIG. 1 were compared with similar results eleven years later (FIG. 2). In this histogram a number of isolates now appear, which have inhibition zones all the way down to no zone, the size of the 6 mm disk. The comparison was accomplished by means of computer analysis according to the inventive method for calibrating antimicrobic susceptibility testings of microorganisms.

First, the slope downwards was tracked and the shift to decreasing values at the peak position identified by comparing sliding means (each based on two zone diameter figures). Then, the percentages of the isolates of the upper half of the population were determined and converted to probit values. A regression using the least squares method was then performed and the theoretical percentages for the whole population calculated. The histograms with the calculated theoretical curves interposed are shown in FIGS. 3 and 4, respectively.

The mean value of the initially measured histogram data from 1988 (FIG. 3) was first calculated according to a customary statistical procedure and was found to be 29.16 mm (SD 3.22). When the same histogram then was analyzed as a normalized Gaussian distribution of a theoretical normal population by means of the method according to the invention, the corresponding mean was found to be 29.27 mm with a standard deviation (SD) of 3.25. The total number of isolates was 3756.

Eleven years later the mean value of all 5944 isolates (FIG. 4) was found to be 28.24 mm (SD 7.39) according to the customary statistical procedure. The normalized Gaussian distribution of a theoretical normal population, however, exhibited a mean value of 30.49 mm with a standard deviation (SD) of 3.22. Thus, the occurrence of resistant strains with low zone values is reflected by the increase in standard deviation for the mean of all strains as well as by a slightly lower mean value.

When the calculated theoretical reference population of normal isolates was used to set a limit for resistance, the 1988 limit was 19 mm and the 1999 year limit for resistance was 20 mm. Thus, the slight shift in the position of the peak during these 11 years is automatically observed and corrections are included in the zone breakpoints for comparative analysis of resistance. The percent resistance for these two populations would then be 0.56% for the 1988 population and 10.8 for the 1999 population, an increase which is in agreement with the true findings.

In this calculation, it is assumed that 3 SD below the mean includes 99.86 percent of the normally susceptible strains in this group. A suitable limit for susceptibility interpretation and comparative analysis of antimicrobic resistance could then be defined as three times the standard deviation below the mean value.

Although the two histograms from 1988 and 1999 exhibit considerable differences, the present method of histogram normalization produced an internal calibration (standardization) of the test, which will permit a comparative analysis of resistance. Thus, the theoretical curve with its mean value and standard deviation can be used for setting a breakpoint, which will not be affected by interlaboratory differences. Nor will the breakpoint be affected by the different frequencies of resistant isolates, which appear in different histograms.

In spite of several years of data collection from antimicrobic susceptibility testings of microorganisms in many centers worldwide, a method has not yet been provided whereby results form different laboratories can be compared. The inventive method makes it possible to utilize the worldwide abundance of for example results from disk diffusion tests, which cannot be utilized for surveillance because of lack of comparability of the data. Furthermore, the invention satisfies the urgent need for another method to "calibrate" the test or to "normalize" the susceptibility test results for comparative purposes. The increasing number of exceptions to the regular zone breakpoints in the NCCLS list verifies this need.

In addition, additional control or reference strains are not necessary for calibration and normalization of the interpretation. All disk test results all over the world can be made comparable and be included in surveillance studies by means of the method according to the invention.

Example 2

A Comparison Between Different Laboratories

The potential of the present invention, whereby results from laboratories in different-parts of the world are comparable.

In this example histograms of zone diameter values from disk test results for *E. coli* tested against the antibiotic gentamicin were analyzed according to the principle of normalized resistance interpretation. One laboratory (KS) used the SRGA (Swedish Reference Group for Antibiotics) methodology and a disk content of 10 μg gentamicin, whereas the other laboratory on a different continent (AR, a clinical microbiology laboratory in South America) used the NCCLS (National Committee for Clinical Laboratory Standards) standardization and a 5 μg gentamicin disk.

Figure 5:
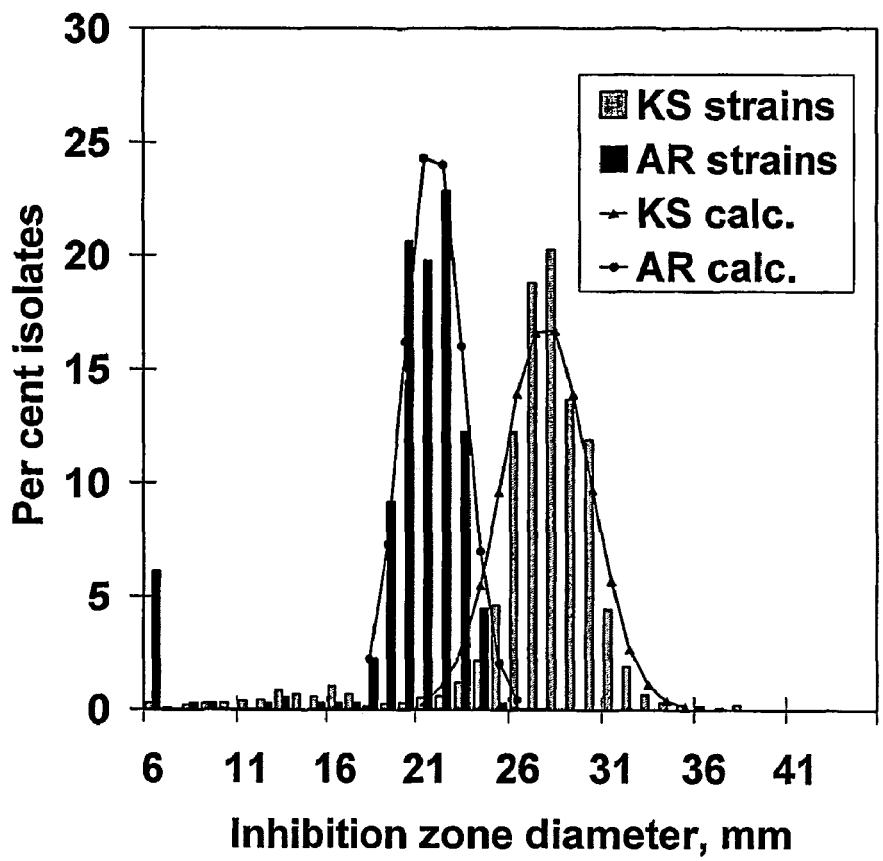
FIG. 5 shows isolates of *E. coli* tested against gentamicin in two different laboratories with interposed calculated normalized distributions.

The different methods used result in different positionings of the major, susceptible populations of strains (FIG. 5). As seen, the method according to the present invention results in two completely different normalized distributions. Consequently, different R-limits for resistance are obtained, i.e. KS: R<21 mm and AR: R<17 mm, respectively. These zone breakpoints for normalized interpretation reflect the true situation with reference to gentamicin resistance in the two laboratories.

Example 3

A Comparison Between True and Calculated Means for the Validation of the Inventive Normalization procedure The inventive method of normalized calculation of a susceptible population of a given bacterial species was validated by using results obtained from repeated tests of reference strains. In this connection it is a normal procedure every day in a clinical microbiology laboratory to test so called control or reference strains, for example *Staphylococcus aureus*, ATCC 29213, and *Escherichia coli*, ATCC 25922 (ATCC=American Type Culture Collection), in disk diffusion tests with reference to their antibiotic susceptibility. The inhibition zone diameter values obtained from each such an individual reference strain form a statistical normal distribution. Thus, the mean value and standard deviation can be calculated directly from the experimental results obtained.

The true mean values from the control strains were compared with the results obtained from corresponding laboratory strains by means of normalized calculations according to the present invention, only the high zone values in the histograms being used.

Figure 6:
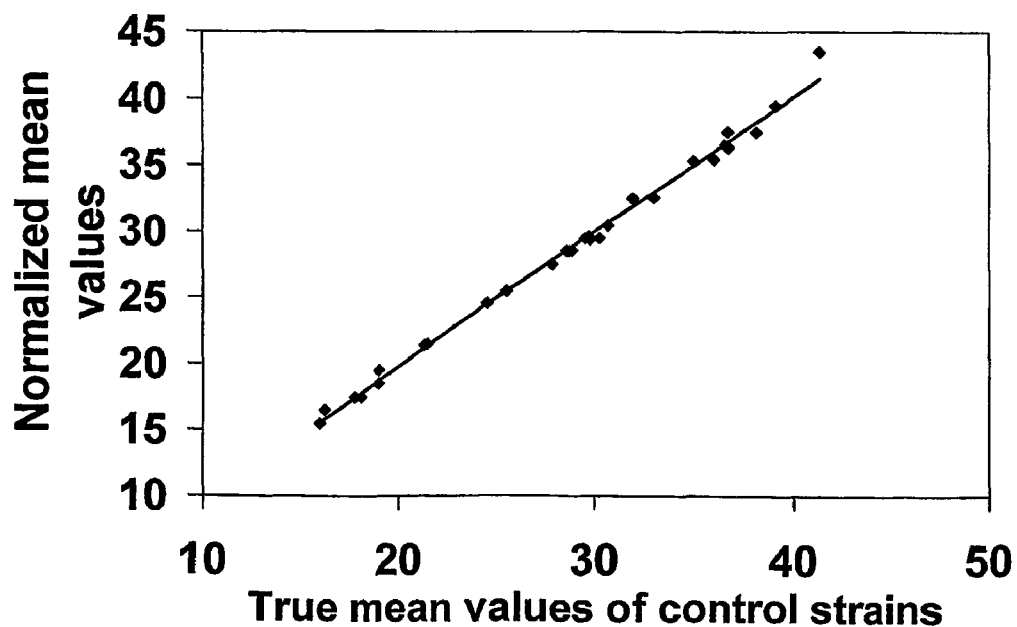
FIG. 6 shows a graph of normalized mean values versus true mean values of control strains.

As shown in FIG. 6, a very close correlation between the true means of the reference bacterial species and the calculated normalized means from corresponding laboratory strains was obtained with a correlation coefficient r=0.998.

The invention claimed is:

1. A method for calibrating antimicrobic susceptibility testing data of microorganisms, wherein the method comprises the steps of creating a histogram based on in vitro susceptibility test data against an antimicrobial agent for isolates from a microbial species, which microbial species isolates may contain unknown resistant strains against said antimicrobial agent wherein the number of isolates of microbial species or percentage of the total number of isolates of microbial species is on a y-axis of said histogram and registered response values against said antimicrobial agent on a x-axis of said histogram;

determining a position of a response peak of the histogram between a high response side and a low response side corresponding to isolates of microbial species susceptible to said antimicrobial agent;

calculating from said high response side of said histogram at least one statistical parameter; and defining a limit for susceptibility interpretation and comparative analysis of antimicrobic resistance, which is based on said at least one statistical parameter; said limit separating susceptible strains from resistant strains against said antimicrobial agent.

2. Method as in claim 1, wherein said isolates are clinical isolates.

3. Method as in claim 1, wherein said at least one statistical parameter is statistically obtained from a probability distribution calculated from said high response side of said histogram.

4. Method as in claim 1, wherein said microbial species is a bacterial species or a fungal species.

5. Method as in claim 1, wherein said antimicrobial agent is an antibiotic.

6. Method as in claim 1, wherein said antimicrobic susceptibility testing is a Minimal Inhibitory Concentration test, said registered response values being minimal inhibitory concentrations.

7. Method as in claim 1, wherein said antimicrobic susceptibility testing is a disk diffusion test, said registered response values being inhibition zone diameter values from paper disks impregnated with said antimicrobial agent.

8. Method as in claim 3, wherein said probability distribution is a Gaussian distribution.

9. Method as in claim 8, wherein said at least one statistical parameter is the mean, defining a position of the statistical response peak between a high statistical response distribution side and a low statistical response distribution side, and/or standard deviation.

10. Method as in claim 9, wherein said limit is defined as three times said standard deviation below said mean.

11. Method as in claim 9, wherein said Gaussian distribution is a standard Gaussian distribution.

12. Method as in claim 9, wherein said Gaussian distribution is a normalized Gaussian distribution of a theoretical normal population.

13. Method as in claim 12, wherein said normalized Gaussian distribution is construed from said position of said statistical response peak, said high statistical response distribution side, and its mirror image.

14. Method as in claim 12, wherein a total number for said theoretical normal population is construed by a procedure comprising the steps of calculating a slope for a line through said number of isolates of adjacent registered response values starting on said high response distribution side;

detecting a shift in slope direction, which represents the position of said statistical response peak, thereby defining said mean; and calculating said total number as the doubled sum of half the number of isolates at said position plus the number of isolates having higher response values.

15. Method as in claim 13, wherein said normalized Gaussian distribution is construed graphically.

16. Method as in claim 14, wherein said normalized Gaussian distribution is determined by a procedure comprising the steps of
- calculating for each registered response value a percentage value as percent of said total number;
- calculating accumulated percentage values for each of said number of isolates or percent isolates on said statistical high response distribution side;
- performing a linearized transformation of said accumulated percentage values against said statistical response values; and
- calculating the equation constants for a linear relationship obtained from said transformation; thereby defining said normalized Gaussian distribution of said theoretical normal population.

17. Method as in claim 15, wherein said graphical construction is performed by means of an undirected graphical model or a directed graphical model.

18. Method as in claim 16, wherein said calculation of equation constants is performed by means of the least squares method.

19. Method as in claim 16, wherein said calculation of accumulated percentage values is performed in the direction 100% to 0%.

20. Method as in claim 16, wherein said transformation k a probit transformation.

21. Method as in claim 20, wherein said standard deviation is calculated from said probit transformation.

* * * * *